(12) United States Patent
Ikudome et al.

(10) Patent No.: US 6,649,794 B2
(45) Date of Patent: Nov. 18, 2003

(54) METHOD FOR PRODUCING 2-HYDROXY-4-METHYLTHIOBUTANOIC ACID

(75) Inventors: Kenji Ikudome, Misawa (JP); Tetsuya Shiozaki, Saijo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/182,836

(22) PCT Filed: Jan. 22, 2000

(86) PCT No.: PCT/JP01/00401

§ 371 (c)(1),
(2), (4) Date: Aug. 2, 2002

(87) PCT Pub. No.: WO01/60791

PCT Pub. Date: Aug. 23, 2001

(65) Prior Publication Data

US 2003/0092934 A1 May 15, 2003

(30) Foreign Application Priority Data

Feb. 18, 2000  (JP) .......................................... 2000-040768

(51) Int. Cl.⁷ ........................ C07C 51/06; C07C 51/08; C07C 51/42
(52) U.S. Cl. ........................................ 562/580; 562/581
(58) Field of Search ................................. 562/580, 581

(56) References Cited

U.S. PATENT DOCUMENTS

| 3,175,000 A | 3/1965 | Gielkens et al. ............. 260/535 |
| 4,524,077 A | 6/1985 | Ruest et al. ................. 514/557 |
| 4,912,257 A | 3/1990 | Hernandez et al. ......... 562/581 |
| 5,856,567 A | 1/1999 | Hsu et al. .................... 562/581 |
| 5,973,198 A | 10/1999 | Shiozaki et al. ............. 562/526 |

FOREIGN PATENT DOCUMENTS

| WO | WO 96/40630 A1 | 12/1996 |
| WO | WO 00/46190 A1 | 8/2000 |

*Primary Examiner*—Peter O'Sullivan
(74) *Attorney, Agent, or Firm*—Sughrue Mion, PLLC

(57) ABSTRACT

A method for producing a 2-hydroxy-4-methylthiobutanoic acid is provided, the method comprising the steps of: hydrolyzing a 2-hydroxy-4-methylthiobutanenitrile and/or a 2-hydroxy-4-methylthiobutanamide in the presence of a sulfuric acid to obtain a reaction mixture containing a 2-hydroxy-4-methylthiobutanoic acid; mixing the reaction mixture with a basic alkaline metal compound to obtain a mixture comprising an oil layer containing the 2-hydroxy-4-methylthiobutanoic acid and a water layer; and separating the oil layer containing the 2-hydroxy-4-methylthiobutanoic acid from the mixture. In accordance with the present invention, a 2-hydroxy-4-methylthiobutanoic acid is obtained with excellent operability and efficiency without using an organic solvent.

5 Claims, No Drawings

METHOD FOR PRODUCING 2-HYDROXY-4-METHYLTHIOBUTANOIC ACID

FIELD OF THE INVENTION

The present invention relates to a method for producing 2-hydroxy-4-metylthiobutanoic acid, which is useful as feed additives and the like. Specifically, the present invention relates to a method for producing 2-hydroxy-4-methylthiobutanoic acid, the method comprising the steps of hydrolyzing 2-hydroxy-4-methylthiobutanenitrile and/or 2-hydroxy-4-metylthiobutanamide in the presence of sulfuric acid.

BACKGROUND OF THE INVENTION

It is known that 2-hydroxy-4-metylthiobutanoic acid is generated by hydrolyzing 2-hydroxy-4-methylthiobutanenitrile or 2-hydroxy-4-metylthiobutanamide in the presence of an acid such as sulfuric acid.

An extraction method using an organic solvent is generally known as a method of separating 2-hydroxy-4-methylthiobutanoic acid from a reaction mixture obtained by hydrolyzing 2-hydroxy-4-methylthiobutanenitrile or 2-hydroxy-4-metylthiobutanamide with sulfuric acid (for example, as disclosed in Japanese Examined Patent Publication No. 5-1787 (1993)). This method, however, has problems such that the cost for product increases and the volumetric efficiency in the production decreases due to the use of the organic solvent, as well as problems in that equipments and operations are required for recovering and purifying the organic solvent and for removing the organic solvent from a produced product and a waste water.

In contrast to the above, a method not using an organic solvent has been proposed wherein a reaction mixture is neutralized with ammonia and the resulting mixture is separated into an oil layer and a water layer (see, U.S. Pat. No. 4,912,257 publication). However, this method has problems such that the separatability between the oil layer and the water layer is poor, a large amount of 2-hydroxy-4-methylthiobutanoic acid layer remains in the water layer, resulting in poor efficiency in extraction of 2-hydroxy-4-methylthiobutanoic acid from the reaction mixture.

SUMMARY OF THE INVENTION

It is an object of the present invention to provide a method for producing 2-hydroxy-4-methylthiobutanoic acid with excellent operability and efficiency without using an organic solvent, which solves the above-mentioned problems.

The inventors of the present invention have made special efforts to find that the above object can be achieved by hydrolyzing 2-hydroxy-4-methylthiobutanenitrile and/or 2-hydroxy-4-methylthiobutanamide in the presence of sulfuric acid and post-treating the resulting reaction mixture in a certain manner, and have finally accomplished the above object to complete the present invention.

That is, the present invention provides a method for producing a 2-hydroxy-4-methylthiobutanoic acid, the method comprising the steps of:

(A) hydrolyzing at least one selected from a 2-hydroxy-4-methylthiobutanenitrile and a 2-hydroxy-4-methylthiobutanamide in the presence of a sulfuric acid to obtain a reaction mixture containing a 2-hydroxy-4-methylthiobutanoic acid;

(B) mixing the reaction mixture obtained in step (A) with a basic alkaline metal compound to obtain a mixture comprising an oil layer containing the 2-hydroxy-4-methylthiobutanoic acid and a water layer; and (C) separating the oil layer containing the 2-hydroxy-4-methylthiobutanoic acid from the mixture obtained in step (B).

DETAIL DESCRIPTION OF THE INVENTION

A method for producing a 2-hydroxy-4-methylthiobutanoic acid in the present invention comprises step (A) in which at least one selected from a 2-hydroxy-4-methylthiobutanenitrile and a 2-hydroxy-4-methylthiobutanamide is hydrolyzed in the presence of a sulfuric acid to obtain a reaction mixture containing 2-hydroxy-4-methylthiobutanoic acid. The starting material used herein is a 2-hydroxy-4-methylthiobutanenitrile, a 2-hydroxy-4-methylthiobutanamide or a mixture thereof. Since ammonium salts such as ammonium sulfate and ammonium bisulfate generate in the above hydrolysis reaction, these ammonium salts are also contained in the reaction mixture. The ratio of the generated ammonium sulfate to the generated ammonium bisulfate varies depending on the amount of the sulfuric acid to be used, the reaction ratio and the like.

A 2-hydroxy-4-methylthiobutanenitrile can be obtained, for example, by reacting an acrolein with a methylmercaptan to obtain a 3-methythiopropionaldehyde, which is then reacted with a hydrogen cyanide. A 2-hydroxy-4-methylthiobutanamide can be obtained, for example, by hydration of a 2-hydroxy-4-methylthiobutanenitrile.

In the case of using a 2-hydroxy-4-methylthiobutanenitrile as a starting material, the hydrolysis reaction to a 2-hydroxy-4-methylthiobutanoic acid comprises a hydration reaction of 2-hydroxy-4-methylthiobutanenitrile to 2-hydroxy-4-methylthiobutanamide and a hydrolysis reaction of the 2-hydroxy-4-methylthiobutanamide to 2-hydroxy-4-methylthiobutanoic acid. These reactions may be carried out in a single step by a single operation, however, since the optimum conditions thereof differ from each other, these reactions are preferably carried out in two step reactions, i.e., the first step reaction mainly for hydration of 2-hydroxy-4-methylthiobutanenitrile to 2-hydroxy-4-methylthiobutanamide and the second step reaction mainly for hydrolysis of 2-hydroxy-4-methylthiobutanamide to 2-hydroxy-4-methylthiobutanoic acid.

The first step reaction can be carried out by allowing 2-hydroxy-4-methylthiobutanenitrile, sulfuric acid and water to react for 1 hour to 3 hours at the temperature of from 40° C. to 70° C. The amount of sulfuric acid used herein may be 0.5 mol to 1 mol, preferably 0.6 mol to 0.8 mol, based on 1 mol of the 2-hydroxy-4-methylthiobutanenitrile. The amount of water used herein may be 20 parts by weight to 70 parts by weight, preferably 25 parts by weight to 50 parts by weight, based on 100 parts by weight of the 2-hydroxy-4-methylthiobutanenitrile. In mixing 2-hydroxy-4-methylthiobutanenitrile, sulfuric acid and water, the water may be used in the state that the water is mixed with the 2-hydroxy-4-methylthiobutanenitrile or the sulfuric acid in advance, that is, the water is contained in the resulting aqueous 2-hydroxy-4-methylthiobutanenitrile solution or the resulting aqueous sulfuric acid solution to be used. In this case, the aqueous sulfuric acid solution may be added to the aqueous 2-hydroxy-4-methylthiobutanenitrile solution, the aqueous 2-hydroxy-4-methylthiobutanenitrile solution may be added to the aqueous sulfuric acid solution, or both of them may be poured concurrently into a container. Preferably, the aqueous 2-hydroxy-4-methylthiobutanenitrile solution is added to the aqueous sulfuric acid solution.

The second step reaction can be conducted by mixing the reaction mixture obtained in the first step reaction with water and allowing them to react with each other for 2 hours to 6 hours at the temperature of from 90° C. to 130° C. The amount of water to be used for the mixing may be 100 parts by weight to 200 parts by weight based on 100 parts by weight of the sulfuric acid which has been used in the first step reaction. In the mixing thereof, the water may be added to the first step reaction mixture, the first step reaction mixture may be added to the water, or both of them may be poured concurrently to a container.

On the other hand, in the case of using a 2-hydroxy-4-methylthiobutanamide as a starting material, the 2-hydroxy-4-methylthiobutanamide may be mixed with a sulfuric acid and water to allow them to react under the same condition as the condition in the above mentioned second step reaction, thereby obtaining 2-hydroxy-4-methylthiobutanoic acid. Herein, the amount of sulfuric acid to be used may be 0.5 mol to 1 mol, preferably 0.6 mol to 0.8 mol, based on 1 mol of the 2-hydroxy-4-methylthiobutanamide. The amount of water to be used may be 40 by weight to 180 parts by weight, preferably 50 by weight to 140 parts by weight, based on 100 parts by weight of the 2-hydroxy-4-methylthiobutanamide.

In the present invention, instep (B), the reaction mixture obtained instep (A) is mixed with a basic alkaline metal compound to obtain a mixture comprising an oil layer containing a 2-hydroxy-4-methylthiobutanoic acid and a water layer. In the mixing, the basic alkaline metal compound may be added to the reaction mixture, the reaction mixture may be added to the basic alkaline metal compound, or both of them may be poured concurrently to a container. Typically, the mixing is carried out by adding the basic alkaline metal compound to the reaction mixture.

The temperature at the time of mixing in step (B) may be 15° C. to 80° C., and is preferably 30° C. to 70° C. The period of time required for the mixing may be 0.1 hour to 3 hours, and is preferably 0.1 hour to 2 hours. During the mixing, heat of neutralization due to neutralization of the ammonium bisulfate with the basic alkaline metal compound generates, and carbon dioxide gas may generate in the case of using a hydrogen carbonate or a carbonate as the basic alkaline metal compound. Therefore, heat removing or gas drainage may be carried out if necessary in step (B).

Examples of the basic alkaline metal compound to used in step (B) include: sodium salts such as sodium hydroxide, sodium hydrogen carbonate and sodium carbonate; potassium salts such as potassium hydroxide, potassium hydrogen carbonate and potassium carbonate; lithium salts such as lithium hydroxide, lithium hydrogen carbonate and lithium carbonate; and the like. Two or more kinds of the basic alkaline metal compound may be used if necessary. Among the above salts, sodium salts such as sodium hydroxide, sodium hydrogen carbonate and sodium carbonate are preferably used. The basic alkaline metal compound may be used in the solid state or in the form of an aqueous solution thereof.

The amount of the basic alkaline metal compound to be used, based on 1 mol of the ammonium bisulfate contained in the reaction mixture being used, may be 0.5 mol or more, preferably 0.6 mol or more, in terms of the alkaline metal from the viewpoints of the oil/water separatability and of reducing sulfate ions in the product; and may be 1.2 mol or less, preferably 0.8 mol or less, in terms of the alkaline metal from the view point of reducing the kinematic viscosity of the product.

The amount of ammonium bisulfate contained in the reaction mixture obtained in step (A) may be determined by analytically. Alternatively, in the case that the use amount of sulfuric acid in step (A) is more than 0.5 mol and less than 1 mol based on 1 mol of the total amount of the 2-hydroxy-4-methylthiobutanenitrile and the 2-hydroxy-4-methylthiobutanamide both being used in the reaction in step (A), as well as in the case where it is considered that substantially all of the 2-hydroxy-4-methylthiobutanenitrile and the 2-hydroxy-4-methylthiobutanamide have been consumed in the reaction, the amount of ammonium bisulfate contained in the reaction mixture obtained in step (A) can be calculated using the following formula:

The amount of ammonium bisulfate (mol) contained in reaction mixture obtained in step (A)=2×the amount of sulfuric acid (mol) used in step (A)−[the amount of 2-hydroxy-4-methylthiobutanenitrile (mol) used in reaction of step (A)+the amount of 2-hydroxy-4-methylthiobutanamide (mol) used in reaction of step (A)]

On the other hand, the amount of the basic alkaline metal compound to be used may be controlled by means of the hydrogen-ion concentration (pH) of the mixture obtained in step (B). For example, when 0.6 mol to 0.8 mol of sodium hydroxide is used based on 1 mol of ammonium bisulfate, pH of the resulting mixture will be about 1.4 to about 1.9 at 25° C., and about 1.9 to about 2.2 at 60° C.

In the present invention, in step (C), the oil layer containing a 2-hydroxy-4-methylthiobutanoic acid is separated from the mixture obtained in step (B) by an operation such that the mixture is maintained still, or is subjected to centrifugation or the like to be separated into the oil layer and the water layer. Inorganic salts may precipitate in the water layer depending on the amount of inorganic salts contained in the water layer and the temperature at the time of the separation. In such a case, oil/water separation may be conducted directly, oil/water separation may be conducted after dissolving the precipitated inorganic salts by heating, or oil/water separation may be conducted after removing the precipitated inorganic salts by filtration or decantation. The temperature at the time of the oil/water separation may be in the range of from 30° C. to 80° C.

The oil layer obtained in step (C) may contain 40% by weight to 60% by weight of 2-hydroxy-4- methylthiobutanoic acid, 20% by weight to 30% by weight of water and 10% by weight to 30% by weight of inorganic salts, although the amounts vary depending on the conditions of the steps (A) to (C). For obtaining the product from the oil layer, though being variable depending on the form and quality of the required product, it is preferred that a step (D) for removing water by concentrating the oil layer is performed, followed by a step (E) for removing insoluble matters such as inorganic salts precipitated at the time of the concentration from the obtained concentrate liquid, in the case where higher concentration of 2-hydroxy-4-methylthiobutanoic acid and reduction in organic salts in the product are requested.

As a condition at the time of the concentration, the temperature may be 30° C. to 90° C., preferably 50° C. to 80° C., and the pressure may be 1 kPa to 20 kPa, preferably 2 kPa to 15 kPa. From the viewpoints of reducing the concentration of sulfate ion in the product obtainable after removal (mentioned below) of the insoluble matters and of reducing the kinetic viscosity of the product, the water content of the liquid phase in the concentrate liquid is preferably 5% by weight or less, is more preferably 2% by weight or less, and is most preferably 1% by weight or less.

Removal of the insoluble matters from the concentrate liquid (slurry) thus obtained may be carried out by filtration or decantation. In the case that filtration is employed, it is preferred that the filtration is executed after heating from the viewpoint of improving filtration efficiency. The filtration temperature may be in the range of from 50° C. to 80° C. In the case that decantation is employed, it is preferred that the decantation is executed after allowing the insoluble matters to precipitate sufficiently by maintaining still or by centrifugation.

The filtrate obtained by the filtration or the supernatant liquid obtained by the decantation as described above may be subjected, if necessary, to adjustment of concentrations of components therein or to other processes, whereby obtaining a product of 2-hydroxy-4-methilthiobutanoic acid which is useful as feed additives or the like. The quality of the product is affected by the conditions in each step described above. For example, when the use amount of the basic alkaline metal compound in step (B) is 0.6 mol to 0.8 mol in terms of the alkaline metal based on 1 mol of ammonium bisulfate in the reaction mixture, and the water content of the liquid phase in the concentrate liquid obtained in step (D) is 2%by weight or less, it is possible to obtain a product of which concentration of sulfate ion is 1% or less and the kinetic viscosity thereof is 100 mm$^2$/S or less.

Since the above-mentioned insoluble matters removed by the filtration or the decantation can typically bear 2-hydroxy-4-methylthiobutanoic acid adhered on their surface or contain the same inside thereof, in order to collect them, the whole or a part of the insoluble matters is preferably added to either one of the above steps (A) to (D) for recycling. In such a case, the insoluble matters may be washed with water to elute 2-hydroxy-4-methylthiobutanoic acid and the aqueous solution obtained here may be recycled.

For disposing byproducts (waste products) such as a water layer and inorganic salts generated in the production method of the present invention, for example, for disposing ammonium sulfate and ammonium bisulfate, an excess amount of sodium hydroxide is added to them and the generating ammonia gas is removed, thereby enabling disposal in the form of sodium sulfate which gives small environmental load.

As described above, in accordance with the present invention, a 2-hydroxy-4-methylthiobutanoic acid is obtained from the reaction mixture of hydrolysis with sulfuric acid of 2-hydroxy-4-methylthiobutanenitrile and/or 2-hydroxy-4-methylthiobutanamide with excellent operability and efficiency without using an organic solvent.

EXAMPLES

The present invention is described by reference to the following Examples, which should not be construed as a limitation upon the scope of the present invention.

Example 1 and Comparative Examples 1 and 2

Into 40.1 g (0.35 mol) of 85.6% by weight of an aqueous sulfuric acid solution, 82.7 g (0.50 mol) of 79.2% by weight of an aqueous 2-hydroxy-4-methylthiobutanenitrile solution was dropped at 50° C. under stirring over 30 minutes, and the resulting mixture was maintained for 2 hours at 50° C. Into the mixture, 57.2 g of water was added, and then, the mixture stirred for 4 hours at 110° C. As a result of analysis of the resulting reaction mixture, the yield of 2-hydroxy-4-methithiobutanoic acid was determined to be 95% to 96%.

Example 1: After adding 8.0 g (0.20 mol) of particulate sodium hydroxide to a reaction mixture obtained in the same manner as described above, the resulting reaction mixture was stirred and was separated into an oil layer and a water layer.

Comparative Example 1: Extraction was conducted by adding 200 g of methylisobutylketone to a reaction mixture obtained in the same manner as described above, and the resulting reaction mixture was separated into an oil layer and a water layer.

Comparative Example 2: Into the reaction mixture obtained in the same method as described above, 13.6 g (0.20 mol) of a 25% aqueous ammonium solution was added, and the resulting reaction mixture was stirred and was separated into an oil layer and a water layer (slurry layer).

Each water layer obtained in the above each operation was analyzed by liquid chromatography and the residual amount of 2-hydroxy-4-methylthiobutanoic acid in the water layer was determined. The results are shown in Table 1.

TABLE 1

|  | | 2-Hydroxy-4-methylthiobutanoic acid | |
| --- | --- | --- | --- |
|  | Water layer Weight (g) | Concentration (%) | Yield (%) |
| Example 1 | 72.0 | 1.26 | 1.21 |
| Comparative Example 1 | 104.6 | 2.08 | 2.90 |
| Comparative Example 2 | 87.0 | 6.60 | 7.65 |

Example 2-1 to Example 2-15

The reaction was carried out in the same manner as in Example 1, and to each of the obtained reaction mixtures (180 g), a specific amount (shown in the Table 2) of 48% by weight of an aqueous sodium hydroxide solution was added respectively, and the resulting mixtures were thoroughly stirred. The pH values at 25° C. of the obtained mixtures are shown in Table 2. Each mixture was separated into an oil layer and a water layer at 60° C. Each oil layer was concentrated by means of an evaporator until the water content (measured by Karl Fischer method) of the liquid phase of the oil layer reaches the value shown in Table 2. Each resulting concentrate liquid (slurry) thus obtained was filtered at 70° C. Into each filtrate thus obtained, water was added so that the content of 2-hydroxy-4-methylthiobutanoic acid is 89.0% by weight (measured by potentiometric titration) to achieve each product.

Concentration of sulfate ion measured by an ion chromatography and kinetic viscosity at 25° C. measured by a Cannon-Fenske viscometer, of each product, are shown in Table 2.

TABLE 2

| Example | Amount to be added of 48% NaOH (g) | (mol) | pH (25° C.) | Water content (%) | Concentration of $SO_4^{2-}$ (%) | Kinetic viscosity (cSt*) |
|---|---|---|---|---|---|---|
| 2-1 | 16.7 | 0.200 | 2.31 | 3.44 | 0.66 | 125.3 |
| 2-2 | 16.7 | 0.200 | 2.31 | 2.76 | 0.57 | 134.2 |
| 2-3 | 16.7 | 0.200 | 2.31 | 2.20 | 0.48 | 116.6 |
| 2-4 | 16.7 | 0.200 | 2.31 | 1.58 | 0.43 | 119.8 |
| 2-5 | 16.7 | 0.200 | 2.31 | 0.75 | 0.40 | 112.1 |
| 2-6 | 16.2 | 0.194 | 2.05 | 2.93 | 0.82 | 112.3 |
| 2-7 | 16.2 | 0.194 | 2.05 | 2.09 | 0.72 | 107.3 |
| 2-8 | 16.2 | 0.194 | 2.05 | 0.74 | 0.53 | 95.9 |
| 2-9 | 14.5 | 0.174 | 1.85 | 2.64 | 1.00 | 104.4 |
| 2-10 | 14.5 | 0.174 | 1.85 | 1.36 | 0.89 | 94.5 |
| 2-11 | 14.5 | 0.174 | 1.85 | 1.10 | 0.68 | 79.3 |
| 2-12 | 12.7 | 0.152 | 1.62 | 2.27 | 1.57 | 120.5 |
| 2-13 | 12.7 | 0.152 | 1.62 | 1.27 | 1.23 | 92.1 |
| 2-14 | 10.9 | 0.131 | 1.44 | 1.44 | 1.20 | — |
| 2-15 | 10.9 | 0.131 | 1.44 | 0.63 | 0.99 | 95.7 |

*1 cSt = 1 $mm^2/s$

Example 3

The following operations (i) to (iv) were repeated for 7 times.

(i) Into 80.5 g (0.7 mol) of 85.2% by weight of an aqueous sulfuric acid solution, 165.0 g (1.0 mol) of 79.2% by weight of an aqueous 2-hydroxy-4-methylthiobutanenitrile solution was dropped over 30 minutes under stirring at 50° C., and the resulting mixture was maintained at 50° C. for 2 hours. Into the mixture, 120 g of water was added, and then the resulting mixture was stirred for 4 hours at 110° C.

(ii) Into the reaction mixture obtained in operation (i), the residue obtained in filtration operation(v) was added (while his addition was not done in the first operation (ii)). Into the resulting mixture, 48% by weight of an aqueous sodium hydroxide solution was added in an amount as shown in Table 3 under stirring.

(iii) The mixture obtained in operation (ii) was separated into an oil layer and a water layer at 70° C.

(iv) The oil layer obtained in operation (iii) was concentrated by means of an evaporator until the water content of the liquid phase reaches the value shown in Table 3.

(v) The resulting concentrate liquid (slurry) obtained in operation (iv) was filtered using a glass filter at 70° C. (vi) Water was added to the filtrate obtained in operation (v) so that the content of 2-hydroxy-4-methylthiobutanoic acid is 89.0% by weight (measured by potentiometric titration) to obtain a product.

Concentration of sulfate ion (measured by ion chromatography) and kinetic viscosity at 25° C. (measured by a Cannon-Fenske viscometer), of each product obtained in different times of operations, are shown in Table 3.

TABLE 3

| | Amount to be added of 48% NaOH (g) | (mol) | Water content (%) | Concentration of $SO_4^{2-}$ (%) | Kinetic viscosity (cSt*) | Yield (%) |
|---|---|---|---|---|---|---|
| 1st | 25.0 | 0.300 | 0.68 | 0.80 | 84.6 | 73.1 |
| 2nd | 25.0 | 0.300 | 0.74 | 0.90 | 90.4 | 94.7 |
| 3rd | 24.0 | 0.288 | 0.78 | 0.67 | 86.3 | 88.1 |
| 4th | 20.2 | 0.242 | 0.86 | 1.01 | 93.0 | 97.1 |
| 5th | 20.0 | 0.240 | 0.62 | 0.99 | 91.6 | 89.7 |
| 6th | 20.0 | 0.240 | 0.75 | 0.98 | 88.1 | 103.7 |
| 7th | 20.0 | 0.240 | 0.40 | 0.91 | 86.0 | 95.7 |

*1 cSt = 1 $mm^2/s$

Low yield in the first operations in Example 3 attributes to that 2-hydroxy-4-methylthiobutanoic acid was contained in the filtration residue thereof in an amount corresponding to 20% or more of the yield. Unstable yields of the second and later operations attributes to the unstability in the amount of 2-hydroxy-4-methylthiobutaonoic acid that had been contained in the filtration residue and had been brought into the reaction in each next different operation. An average yield of the reactions of the second to seventh operations is 95%.

What is claimed is:

1. A method for producing a 2-hydroxy-4-methylthiobutanoic acid, the method comprising the steps of:
   (A) hydrolyzing at least one selected from a 2-hydroxy-4-methylthiobutanenitrile and a 2-hydroxy-4-methylthiobutanamide in the presence of a sulfuric acid to obtain a reaction mixture containing a 2-hydroxy-4-methylthiobutanoic acid;
   (B) mixing the reaction mixture obtained in step (A) with a basic alkaline metal compound to obtain a mixture comprising an oil layer containing the 2-hydroxy-4-methylthiobutanoic acid and a water layer; and
   (C) separating the oil layer containing the 2-hydroxy-4-methylthiobutanoic acid from the mixture obtained in step (B).

2. A production method according to claim 1, further comprising the steps of:
   (D) concentrating the oil layer so as to remove water therefrom to obtain a concentrate liquid; and
   (E) removing insoluble matters from the concentrate liquid.

3. A production method according to claim 2, further comprising the step of:
   (F) adding the whole or a part of the insoluble matters obtained in step (E) to any one of steps (A) to (D).

4. A production method according to any one of claims 1 to 3, wherein the basic alkaline metal compound used in step (B) is at least one selected from sodium hydroxide, sodium carbonate and sodium hydrogen carbonate.

5. A production method according to any one of claims 1 to 3, wherein the basic alkaline metal compound is used in step (B) in an amount corresponding to 0.5 mole to 1.2 mol in terms of the alkaline metal, based on 1 mol of the ammonium bisulfate contained in the reaction mixture obtained in step (A).

* * * * *

UNITED STATES PATENT AND TRADEMARK OFFICE
CERTIFICATE OF CORRECTION

PATENT NO. : 6,649,794 B2
DATED : November 18, 2003
INVENTOR(S) : Kenji Ikudome and Tetsuya Shiozaki It is certified that error appears in the above-identified patent and that said Letters Patent is hereby corrected as shown below:

<u>Title page,</u>
Item [22], PCT Filed, please change "Jan. 22, 2000" to -- Jan. 22, 2001".

Signed and Sealed this

Eleventh Day of May, 2004

JON W. DUDAS
*Acting Director of the United States Patent and Trademark Office*